US 6,672,167 B2

(12) United States Patent
Buell et al.

(10) Patent No.: US 6,672,167 B2
(45) Date of Patent: Jan. 6, 2004

(54) METHOD AND SYSTEM FOR PROCESSING LASER VIBROMETRY DATA EMPLOYING BAYESIAN STATISTICAL PROCESSING TECHNIQUES

(75) Inventors: Walter F. Buell, Redondo Beach, CA (US); Bradley A. Shadwick, Berkeley, CA (US)

(73) Assignees: The Aerospace Corporation, El Segundo, CA (US); The Institute for Advanced Physics, Conifer, CA (US)

( * ) Notice: Subject to any disclaimer, the term of this patent is extended or adjusted under 35 U.S.C. 154(b) by 0 days.

(21) Appl. No.: 09/841,045

(22) Filed: Apr. 23, 2001

(65) Prior Publication Data

US 2003/0010128 A1 Jan. 16, 2003

(51) Int. Cl.[7] .......................... G01N 29/04; G06F 19/00
(52) U.S. Cl. .............................. 73/657; 73/602; 73/655; 702/56
(58) Field of Search ...................... 73/579, 655, 656, 73/597, 598, 599, 600, 602, 657; 356/349, 351; 702/56

(56) References Cited

U.S. PATENT DOCUMENTS

| | | | | |
|---|---|---|---|---|
| 5,170,666 A | * | 12/1992 | Larsen | 73/571 |
| 5,233,541 A | * | 8/1993 | Corwin et al. | 348/81 |
| 5,673,110 A | * | 9/1997 | Erickson et al. | 356/357 |
| 5,821,424 A | * | 10/1998 | Rodriguez | 73/657 |
| 5,841,030 A | * | 11/1998 | Honsberg et al. | 73/579 |
| 6,007,494 A | * | 12/1999 | Zenner et al. | 600/559 |
| 6,122,601 A | * | 9/2000 | Swanson et al. | 702/137 |
| 6,320,665 B1 | * | 11/2001 | Ngoi et al. | 356/485 |
| 6,381,555 B1 | * | 4/2002 | Sewell | 702/181 |

OTHER PUBLICATIONS

G. L. Bretthorst, *Bayesian Spectrum Analysis and Parameter Estimation*, Lecture Notes in Statistics, vol. 48, Springer-Verlag, New York, 1988.

\* cited by examiner

*Primary Examiner*—Hezron Williams
*Assistant Examiner*—Jacques Saint-Surin
(74) *Attorney, Agent, or Firm*—Henricks, Slavin & Holmes LLP

(57) ABSTRACT

A method and system for processing laser vibrometry data are embodied in a processor configured to employ a statistical signal processing technique (e.g., a Bayesian processing technique) to process one or more mathematical models, laser vibrometry data for a system under observation, and prior information to generate estimates of parameters for the one or more mathematical models.

14 Claims, 6 Drawing Sheets

32 μs window

| $f$ [Hz] | $B_1$ [kHz] | $B_2$ [kHz] | $|B|$ [kHz] |
|---|---|---|---|
| 8.67 ± 0.51 | -1.857 | -0.711 | 1.989 |
| 22.08 ± 0.11 | -5.733 | 5.850 | 8.191 |
| 36.30 ± 0.57 | 0.925 | -1.216 | 1.528 |
| 42.73 ± 0.49 | -2.257 | 0.966 | 2.455 |
| 57.37 ± 0.41 | 1.913 | 0.352 | 1.945 |

FIG. 5A

64 μs window

| $f$ [Hz] | $B_1$ [kHz] | $B_2$ [kHz] | $|B|$ [kHz] |
|---|---|---|---|
| 8.79 ± 0.56 | -1.718 | -0.497 | 1.788 |
| 21.70 ± 0.13 | -5.021 | 6.004 | 7.826 |
| 35.52 ± 0.74 | 0.261 | -1.347 | 1.372 |
| 42.43 ± 0.67 | -1.475 | 1.682 | 2.237 |
| 57.74 ± 0.50 | 1.743 | -0.196 | 1.754 |

FIG. 5B

128 μs window

| $f$ [Hz] | $B_1$ [kHz] | $B_2$ [kHz] | $|B|$ [kHz] |
|---|---|---|---|
| 8.88 ± 0.68 | -1.726 | -0.882 | 1.938 |
| 21.70 ± 0.16 | -5.124 | 5.829 | 7.761 |
| 36.64 ± 0.73 | 0.819 | -1.246 | 1.491 |
| 43.14 ± 0.64 | -2.244 | 1.077 | 2.489 |
| 58.03 ± 0.56 | 1.730 | 0.356 | 1.766 |

FIG. 5C

256 μs window

| $f$ [Hz] | $B_1$ [kHz] | $B_2$ [kHz] | $|B|$ [kHz] |
|---|---|---|---|
| 9.14 ± 1.2 | -0.911 | -0.945 | 1.313 |
| 21.87 ± .21 | -5.562 | 5.543 | 7.853 |
| 35.88 ± .77 | 0.639 | -1.713 | 1.828 |
| 43.42 ± .70 | -2.657 | 0.906 | 2.808 |
| 58.31 ± 1.1 | 1.246 | 0.428 | 1.317 |

FIG. 5D

METHOD AND SYSTEM FOR PROCESSING LASER VIBROMETRY DATA EMPLOYING BAYESIAN STATISTICAL PROCESSING TECHNIQUES

BACKGROUND OF THE INVENTION

1. Field of Invention

The present invention relates generally to a laser vibrometry method and system and, more specifically, to a method and system for processing laser vibrometry data employing Bayesian statistical processing techniques.

2. Description of the Related Art

Laser vibrometry (LV) provides a sensitive non-contact means of measuring vibrations of objects. In a LV measurement, a laser beam illuminates an object of interest, which may be stationary or in motion, and the returned scattered light is mixed with a local oscillator derived from the same laser or a different laser frequency-referenced to the first. The instantaneous beat frequency provides a measurement of the surface velocity that may be extracted from the time-series data by signal processing (for example, a Fourier transform). The time evolution of the beat frequency then contains information about the state of motion (vibration or other time-varying velocity) of the target, which can be extracted by further processing. Traditional methods for processing LV data include the FM discriminator method, spectrogram processing (a Fourier method), and time-frequency distributions. See, e.g., A. L. Kachelmyer and K. I. Schultz, "Laser vibration sensing," *Linc. Lab. J.* 8(1), pp. 3–28, 1995 and T. D. Cole and A. S. El-Dinary, "Estimation of target vibration spectra from laser radar backscatter using time-frequency distributions," in *Applied Laser Radar Technology, Proc.* SPIE, G. W. Kamerman and W. E. Keicher, eds., vol. 1936, pp. 90–103, SPIE, (Bellingham, Wash.), 1993, both of which are incorporated herein by reference.

Since the development of the Fast Fourier Transform (FFT), discrete Fourier transforms have become for many the first and last word in analyzing the frequency content of a signal. In many circumstances this use of discrete transforms is quite well justified. There are, however, many important instances where the FFT-based approach to spectral estimation is not optimal. One such example is that of short time series. The resolution of the discrete Fourier transforms is determined by the sample duration. When this interval only covers a few periods of the frequency of interest, it can be difficult to obtain good frequency estimates. This difficulty is further exacerbated by the leakage of the spectral response of the data windowing function into the spectral range of the signal. Even if no window function is explicitly applied (a questionable practice in any event) there is an implicit windowing of the data that can not be avoided.

In order to be of utility for laser vibration sensing, a signal processing method must operate well in the presence of noise, be robust to speckle broadening and laser linewidth, and be computationally efficient. It should also yield useful spectra in a small number of vibrational periods, especially when the vibrational period is long or if the measurement time is limited. This latter requirement poses a significant constraint on FFT approaches because the frequency resolution is roughly equal to the inverse of the measurement time. Accordingly, there is a need for a signal processing approach that provides improved performance and resolution for laser vibration sensing.

SUMMARY OF THE INVENTION

According to the present invention, an approach to laser vibrometry data analysis based on statistical inference is employed. Generally, the methods of the present invention (broadly labeled as Maximum Entropy) depart from traditional data-processing approaches in favor of the modeling of experiments. This distinction is more than merely pedantic and allows not only for a sound theoretical basis for estimation of various parameters of interest but also for assignment of confidence levels to these parameter estimates as well as for making relative quantitative assessments between competing models as to which is most consistent with the data.

While the traditional approach to data analysis involves working "backwards" from the measured data to determine the parameters of interest in the model, in an exemplary preferred embodiment of the present invention, data analysis based on Bayesian statistical inference works "forwards" from the model to determine the model most statistically consistent with the data. Thus, the question is asked, "How likely is it that the observed data is a consequence of the model?"

The statistical framework of the present invention allows for much more than the fitting of parameters in the model to match the data. In particular, often there are parameters in models that are essential for describing the data but otherwise do not contain physically relevant information. In a standard fitting approach, these uninteresting parameters would still nonetheless have to be included in along with "interesting" parameters. Moreover, it is not uncommon for these uninteresting parameters to out-number the interesting parameters, making the fitting procedure a great deal more work than if one could somehow consider only the physically relevant parameters. According to the statistical approach of the present invention, it is possible to marginalize (integrate out) these uninteresting parameters (often called nuisance parameters) leaving only the physically important parameters behind. Effectively this facilitates determination of the values of the relevant parameters most consistent with the data knowing that the nuisance parameters will take on whatever values necessary to be consistent with the data. A germane example of nuisance parameters is the phase and quadrature amplitudes of a sinusoidal signal; very often only the frequencies of vibration are of interest. According to the present invention, Bayesian methods provide the framework to consider the important parameters of models of systems under observation while (effectively) ignoring the unimportant parameters. Because of the optimal use of prior knowledge about the laser vibrometry signal provided by the Bayesian statistical signal processing method and system of the present invention, the frequencies can be determined with much greater precision and greater noise immunity than using Fourier- or time-frequency-based approaches. Furthermore, the Bayesian approach of the present invention provides superior performance when the data extends over a small number of vibration periods. The potential advantage of this technique is several orders of magnitude improvement in the precision of the determination of vibrational frequencies, depending upon experimental conditions. An improvement of about a factor of 50 in the precision of the determination of vibrational frequencies has been observed employing the techniques of the present invention.

In accordance with one embodiment of the present invention, a laser vibrometry method includes the steps of: employing a laser to generate laser vibrometry data for a system under observation (e.g., a reflective target); and performing Bayesian parameter estimation calculations for a mathematical model of the system under observation, the laser vibrometry data and prior information to generate estimations of parameters of the mathematical model. In a preferred embodiment, the laser vibrometry method farther includes the steps of evaluating the estimations of parameters; and, if desired or necessary, repeating the step of performing Bayesian parameter estimation calculations with a different model and/or different laser vibrometry data. The laser vibrometry data is, for example, continuous wave (CW) laser vibrometry data, dual pulse coherent laser vibrometry data, or vibrational imaging data. By way of example, the prior information is noise information such as noise information pertaining to a signal-to-noise ratio, or noise information that is assigned a least informative probability density. In a preferred embodiment, the step of evaluating parameter estimation results includes evaluating vibration frequencies. In a preferred embodiment, the step of evaluating parameter estimation results includes evaluating variances of parameter estimates. In a preferred embodiment, the step of evaluating parameter estimation results includes evaluating higher order moments.

In accordance with another embodiment of the present invention, a laser vibrometry method includes the steps of: creating one or more mathematical models of a system under observation; employing a laser to generate laser vibrometry data for the system under observation; and processing the one or more mathematical models, the laser vibrometry data and prior information employing a statistical signal processing technique to generate estimates of parameters for the one or more mathematical models. In a preferred embodiment, the laser vibrometry method further includes the steps of: performing an evaluation of the parameter estimations; and, if results of the evaluation are determined not to be satisfactory, repeating the processing step with a different model and/or different laser vibrometry data. In a preferred embodiment, the statistical signal processing technique employs Bayesian decision theory. In a preferred embodiment, the statistical signal processing technique employs a Bayesian statistical inference technique. In a preferred embodiment, the statistical signal processing technique employs a subjectivist inference technique.

In accordance with another embodiment of the present invention, a system for processing laser vibrometry data includes: a processor configured to employ a statistical signal processing technique to process one or more mathematical models, laser vibrometry data for a system under observation, and prior information to generate estimates of parameters for the one or more mathematical models. In a preferred embodiment, the statistical signal processing technique comprises a Bayesian processing technique. In a preferred embodiment, the one or more mathematical models are models of the system under observation. In a preferred embodiment, the processor is configured to process parameter estimation results to facilitate an evaluation of hypotheses about parameters of a process generating the laser vibrometry data.

The method and system of the present invention are suitable for commercial industrial laser vibrometry, laser velocimetry devices (e.g., fiber-optic blood flow measurement devices), coherent laser processing, and vibrational imaging. Measurements of vibrations of objects can be used in industrial quality control and wear monitoring as well as in the analysis of the vibrational characteristics of objects. Other applications include failure analysis of mechanical devices, identification of objects/machinery, and laser microphones.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings:

FIGS. 5A–5D show frequency and amplitude estimates using various window sizes;

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention.

Figure 8:
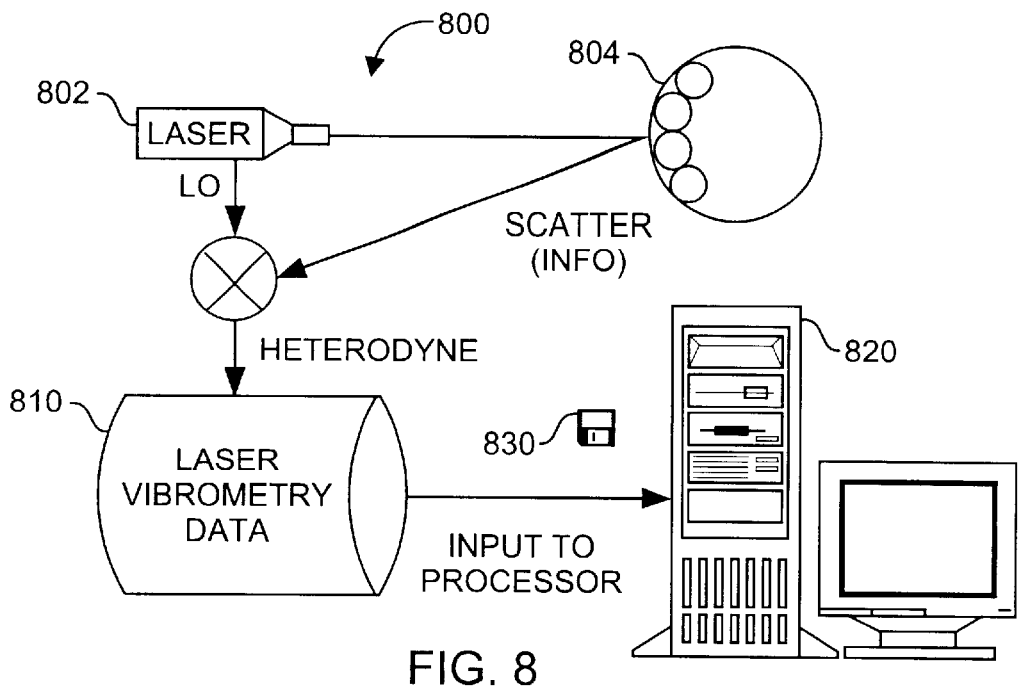
FIG. 8 shows a laser vibrometry system according to an exemplary embodiment of the present invention.

Referring to FIG. 8, an exemplary laser vibrometry system 800 according to the present invention includes a laser 802, a laser vibration sensing device, which generates laser vibrometry data 810, and a processor 820. By way of example, the laser vibrometry data 810 is acquired by directing the output of the laser 802 toward a reflective target 804 (stationary or in motion) as shown. In laser vibrometry, the surface motion is monitored by heterodyne laser Doppler velocimetry, and the received heterodyne signal is sampled to produce a time-series that is processed to obtain a vibrational spectrum of the object under test. A computer-executable program (software) for controlling the processor 820 to implement the processing methods of the present invention is provided to the processor 820 on a computer-readable medium 830 (e.g., a diskette).

Figure 9:
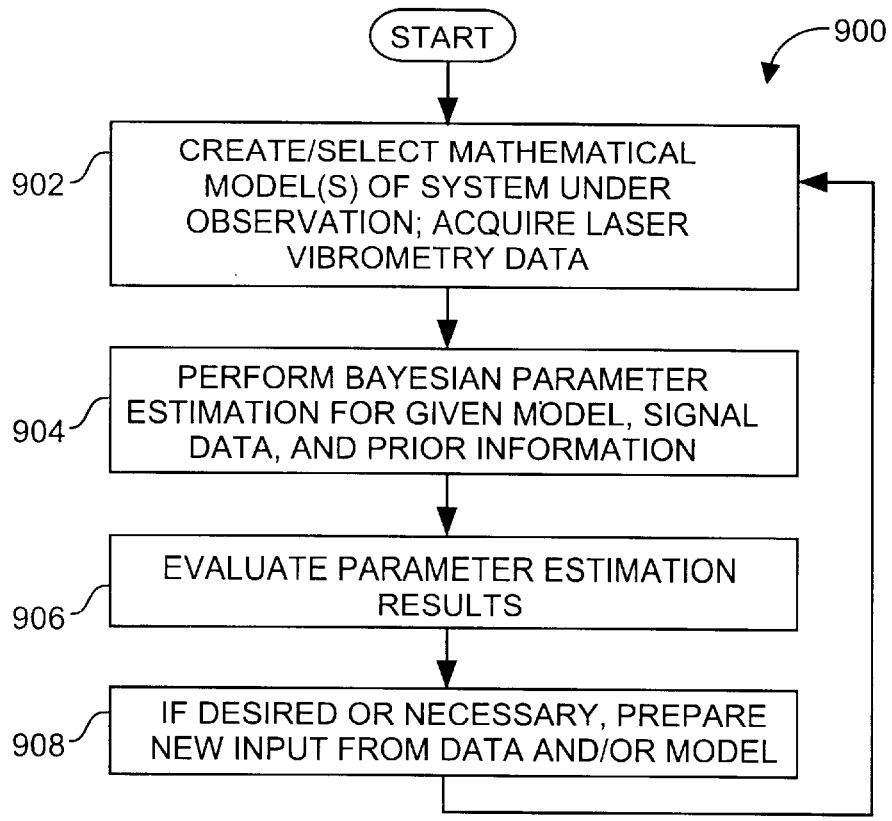
FIG. 9 is a flowchart showing the major steps of a laser vibrometry method according to an exemplary embodiment of the present invention.

Referring to FIG. 9, an exemplary laser vibrometry method 900 according to the present invention includes a step 902 of creating/selecting mathematical model(s) of a system under observation and acquiring laser vibrometry data. Next, at step 904, the processor 820 is employed to perform a Bayesian parameter estimation for a given model, signal data, and prior information. At step 906, the parameter estimation results are evaluated. If desired or necessary, at step 908, new data and/or model inputs to processing step 904 are prepared. Observed results of and additional details pertaining to the method and system of the present invention are presented below.

Figure 1:
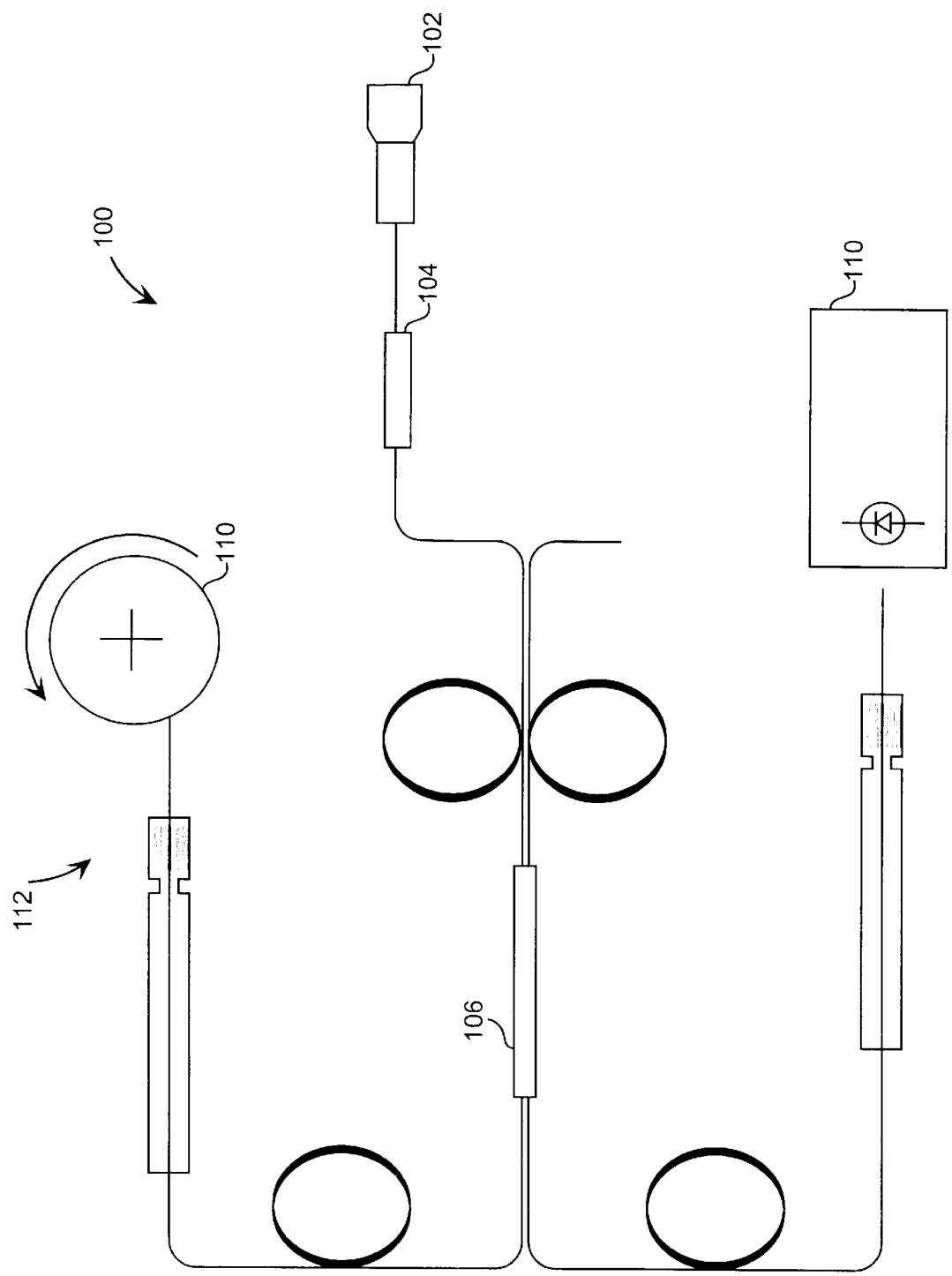
FIG. 1 shows an experimental setup for fiber-optic laser Doppler velocimeter.

The employment of Bayesian frequency estimation according to the present invention has been observed to dramatically outperform the FFT approach when determining the vibrational frequency. To evaluate the performance of the statistical processing methods of the present invention, data from a fiber-optic laser Doppler velocimeter developed for in situ fluid flow measurements was used. Referring to FIG. 1, the experimental arrangement 100 included a transmitter 102, an optical isolator 104, a fiber-optic coupler 106, a target 108 and a detector/amplifier 110 optically interconnected as shown. In the experiment, the target 108 was a rotating wheel coated with a diffuse reflecting surface and driven with an optical chopper-wheel motor.

The transmitter 102 was a Hitachi ML776H11F InGaAsP distributed feedback, multi-quantum-well diode laser, of wavelength $\lambda=1.31\ \mu m$, nominal power $P_O=5$ mW, pigtailed to SMF28 single mode fiber. A low noise, constant current supply provided an injection current of 13.7 mA to the diode laser. No temperature control or external wavelength stabilization was employed.

The fiber-optic coupler 106 was a 2×2 fiber-optic coupler (CANSTAR DBS-02×02-131/155-50) with a 47.7%/52.3% coupling ratio employed to direct 52.3% of the laser output, or P=0.63 mW, onto the rotating wheel target with reflectivity R~50%. In order to simulate a well-defined vibration frequency, the voltage drive to the wheel motor was sinusoidally modulated at a frequency near 20 Hz, resulting in a modulation of the wheel's angular velocity. The transceiver end 112 of the fiber was cleaved normal to the fiber, positioned 1.38 cm below, and 1.37 cm laterally from the center of the 3.56 cm diameter wheel. The end of the fiber was thus z=2.4 mm from the center of the illuminated spot on the wheel. For the data analyzed here, the mean surface velocity component along the laser beam was about 10 cm/s, corresponding to a Doppler shift of approximately 200 kHz. The fiber nominally has a 9.3 $\mu m$ mode field diameter and a numerical aperture of 0.13.

The backscattered signal was collected back into the fiber, transmitted through the other angle-cleaved, coupler input and directed onto an Epitax ETX300T InGaAs PIN photodiode (quantum efficiency $\eta=0.8$), which was AC-coupled to a low noise transimpedance amplifier (Analog Modules 711-4-4-AC). The detector/amplifier combination 110 has a bandwidth B=1.5 MHz, 2.9 pW/Hz$^{1/2}$ noise, and was operated with a transimpedance gain of approximately 3 V/$\mu$W. Voltage waveforms were collected at 2 megasample/s using a 12-bit, ±1 V full scale A/D card (Adlink AD9812). Each sampled waveform consists of 216, 136 contiguous points, or 0.108 seconds of data (thus allowing about 2.4 vibrational periods).

The carrier-to-noise ratio (CNR) can be estimated as $$CNR = \frac{P\lambda}{hcB}\frac{A}{z^2}T^2 R\eta\cos\theta, \qquad (1)$$

where A is the fiber core cross-sectional area and $\theta$ is the scattering angle. With the parameters given above, and assuming 20% optical transmission efficiency T (including reflection losses, coupler losses and coupling to the detector) a CNR of about 20 dB can be expected. This can be considered the high CNR regime.

Figure 2:
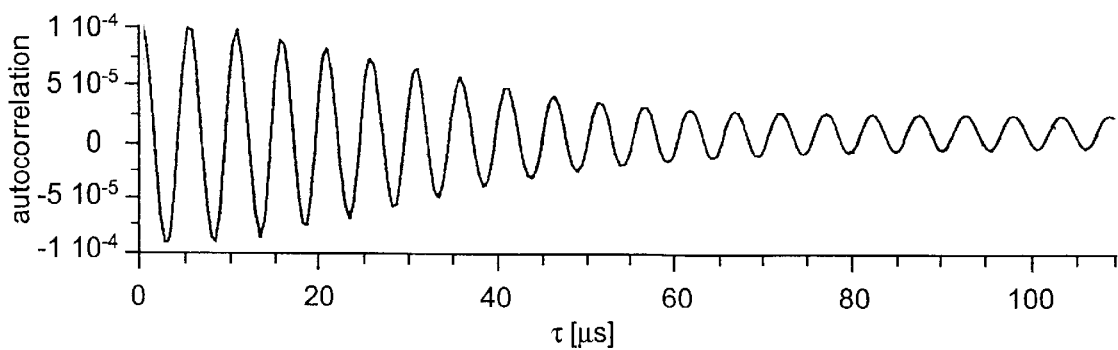
FIG. 2 is a plot showing autocorrelation of the Doppler signal for the experimental setup of FIG. 1.

The purpose for selecting the rotating wheel geometry was both to provide a velocity offset for a reasonable Doppler carrier frequency (without frequency-shifting the local oscillator) and to provide a reasonable amount of speckle broadening for testing the robustness of the signal processing methods. The combined effect of speckle broadening and laser phase noise can be determined from the autocorrelation function of the experimental data as illustrated in FIG. 2. The envelope is roughly Gaussian with a 1/e width of 40 $\mu s$, for a coherence bandwidth of about 25 kHz. An overview of the statistical processing methods of the present invention and their implementation is presented below.

The goal of Bayesian data analysis is to evaluate the conditional probability of values for the parameters in the model given the data and any prior information. See, e.g., G. L. Bretthorst, *Bayesian Spectrum Analysis and Parameter Estimation*, Lecture Notes in Statistics, volume 48, Springer-Verlag, New York, 1988, which is incorporated herein by reference. Formally, through the use of Bayes' theorem $$P(\upsilon\mid\partial,\mathcal{I}) = \frac{P(\upsilon\mid\mathcal{I})P(\partial\mid\upsilon,\mathcal{I})}{P(\partial\mid\mathcal{I})} \qquad (2)$$

where $\upsilon$ denotes the set of parameters in the model, $\mathcal{I}$ presents the prior information, and $\partial$ represents the measured data. Here, $P(\upsilon|\partial,\mathcal{I})$ is the posterior probability of the model parameters given the data and prior information. This is the quantity of interest—the "best" values of the parameters are those that maximize this probability. The remaining terms in (2) have the following interpretations: $P(\upsilon|\mathcal{I})$ is the probability of the parameters given only the prior information; $P(\partial|\mathcal{I})$ is the probability of the data given the prior information; and $P(\partial|\upsilon,\mathcal{I})$ is the probability of the data given the parameters and prior information (this is often referred to as the likelihood of the data). For a given model and data set, $P(\partial|\mathcal{I})$ can be considered a normalization constant. It is only of interest in comparing the relative probability of different models.

The prior probability of the parameters, $P(\upsilon|\mathcal{I})$, is meant to summarize knowledge of the model parameters before the experiment is performed. As long as there is sufficient data, the choice of this prior will have little influence on the final probability. A conservative approach is to choose a prior that represents "complete ignorance" regarding the parameter values. The choice of the priors is discussed more specifically below when the specific model representing the time series is examined.

The likelihood of the data is perhaps conceptually the most straightforward part of the calculation. The discrete set of N data samples is denoted as $$\partial = \{d_j\}_{j=0}^{N-1},$$

that correspond to the sample times $$\{t_j\}_{j=0}^{N-1}.$$

The measured data is assumed to be described by a model $g(t;\upsilon)$ plus noise $\epsilon(t)$, i.e., $$d_j=g(t_j;\upsilon)+\epsilon(t_j),\ j=0,\ 1,\ 2\ \ldots N{-}1. \qquad (3)$$

Typically, there is little or no information available regarding the measurement noise, yet a prior probability is to somehow be assigned to the noise. Motivated by the principle of maximum entropy, the noise is assigned the least informative probability density, namely:

$$P(\varepsilon | \sigma, \mathcal{J}) = \frac{1}{\sqrt{2\pi\sigma^2}} e^{-\varepsilon^2/2\sigma^2}. \quad (4)$$

Under the assumption that the noise is uncorrelated, the probability that the measurement has the set of noise values $$e = \{\varepsilon_j\}_{j=0}^{N-1} \quad (5)$$

is $$P(e | \sigma, \mathcal{J}) \propto \prod_{j=0}^{N-1} \frac{1}{\sqrt{2\pi\sigma^2}} e^{-\varepsilon_j^2/(2\sigma^2)} \propto$$

$$\sigma^{-N} \exp\left\{-\frac{1}{2\sigma^2} \sum_{j=0}^{N-1} (d_j - g(t_j; \upsilon))^2\right\}.$$

Combining this result with (2) yields $$P(\upsilon | \partial, \mathcal{J}) \propto P(\upsilon | \mathcal{J}) \times \sigma^{-N} \exp\left\{-\frac{1}{2\sigma^2} \sum_{j=0}^{N-1} (d_j - g(t_j; \upsilon))^2\right\}, \quad (6)$$

where the parameter set has been expanded to include the noise variance $\sigma$.

According to an exemplary preferred embodiment of the present invention, Bayesian analysis is employed to extract the vibration spectrum from the time series of Doppler shifts. In this case, there are both a relatively short time series (in terms of the vibration period) and a significant stochastic "noise" component in the signal (in part due to speckle broadening). The determination of a single sinusoidal signal is one example of Bayesian data analysis; the methods disclosed herein are extremely versatile and have wide applicability. Thus, by way of example, the data model is taken to consist of a single harmonic frequency:

$$g(t;\omega, B_1, B_2) = B_1 \cos \omega t + B_2 \sin \omega t. \quad (7)$$

With this model, the posterior probability of the parameters becomes $$P(\omega, B_1, B_2, \sigma | \partial, \mathcal{J}) \propto \quad (8)$$

$$P(\upsilon | \mathcal{J}) \times \sigma^{-N} \exp\left\{-\frac{1}{2\sigma^2} \sum_{j=0}^{N-1} (d_j - B_1 \cos\omega t_j - B_2 \sin\omega t_j)^2\right\}.$$

Treating the phase and quadrature amplitudes as well as the noise variance as nuisance parameters, the marginal probability $P(\omega|\partial,\mathcal{J})$ is considered. Uniform priors are taken for $B_i$ and the so-called Jeffreys prior, $1/\sigma$, is adopted for the noise variance. See, Bretthorst. This provides $$P(\omega|\partial, \mathcal{J}) \propto \quad (9)$$

$$\int d\sigma \int dB_1 B_2 \sigma^{-(N+1)} \exp\left\{-\frac{1}{2\sigma^2} \sum_{j=0}^{N-1} (d_j - B_1 \cos\omega t_j - B_2 \sin\omega t_j)^2\right\}.$$

In this application, the data is uniformly sampled in time. Let $\Delta t$ be the sampling interval and $\Omega = \omega \Delta t$. The argument of the exponential in (9) can then be written as $$-\frac{1}{2\sigma^2} \sum_{j=0}^{N-1} \{d_j^2 + B_1^2 \cos^2 j\Omega + \quad (10)$$

$$B_2^2 \sin^2 j\Omega + B_1 B_2 \sin 2j\Omega - 2B_1 d_j \cos j\Omega -$$
$$2B_2 d_j \sin j\Omega\} =$$
$$N\overline{d^2} + B^T M B - 2B^T b,$$

where $$B = \begin{pmatrix} B_1 \\ B_2 \end{pmatrix}, \quad (11)$$

$$M = \begin{pmatrix} \sum_{j=0}^{N-1} \cos^2 j\Omega & \sum_{j=0}^{N-1} \sin 2j\Omega \\ \sum_{j=0}^{N-1} \sin 2j\Omega & \sum_{j=0}^{N-1} \sin^2 j\Omega \end{pmatrix}, \quad (12)$$

$$b = \begin{pmatrix} \sum_{j=0}^{N-1} d_j \cos j\Omega \\ \sum_{j=0}^{N-1} d_j \sin j\Omega \end{pmatrix}. \quad (13)$$

and $\overline{d^2}$ is the average of $d_j^2$ over the data set. The sums in (12) can be computed in closed form, yielding $$M = \begin{pmatrix} \frac{1}{2}\left[N + \frac{\sin N\Omega \cos(N-1)\Omega}{\sin\Omega}\right] & \frac{1}{2} \frac{\sin N\Omega \sin(N-1)\Omega}{\sin\Omega} \\ \frac{1}{2} \frac{\sin N\Omega \sin(N-1)\Omega}{\sin\Omega} & \frac{1}{2}\left[N - \frac{\sin N\Omega \cos(N-1)\Omega}{\sin\Omega}\right] \end{pmatrix}. \quad (14)$$

According to the present invention, all elements of M in (14) are retained. This is a departure form the conventional practice of discarding the off-diagonal elements and approximating the diagonal elements by N/2. While the procedure of the present invention is more algebraically complex, the final form is no more computationally demanding than that obtained by the aforementioned approximation. Moreover, keeping all terms provides greater accuracy in cases of short data sets.

For $0 < \Omega < \pi$, M has positive definite eigenvalues. Thus, (9) can be written as $$P(\omega | \partial, \mathcal{J}) \propto \int_0^\infty d\sigma \sigma^{-(N+1)} \int_{-\infty}^\infty dB_1 dB_2 e^{-(N\overline{d^2} + B^T M B - 2B^T b)/2\sigma^2}. \quad (15)$$

The Gaussian integral is evaluated by introducing the change of variables $\hat{B} = B - M^{-1}b$. Now $dB_1 dB_2 = d\hat{B}_1 d\hat{B}_2$ and $$\int_{-\infty}^\infty dB_1 dB_2 e^{-(N\overline{d^2} + B^T M B - 2B^T b)/2\sigma^2} = \quad (16)$$

$$e^{-(N\overline{d^2} - b^T M^{-1} b)/2\sigma^2} \int_{-\infty}^\infty d\hat{B}_1 d\hat{B}_2 e^{-\hat{B}^T M \hat{B}/2\sigma^2}.$$

Since M is symmetric, there exists an orthogonal matrix S such that $S^T M S = \text{diag}(\lambda_1, \lambda_2)$. Let $u = S^T \hat{B}$. Since det S=1, (16) becomes $$\int_{-\infty}^{\infty} dB_1 dB_2 e^{-(N\overline{d^2} + B^T MB - 2B^T b)/2\sigma^2} = \quad (17)$$

$$e^{-(N\overline{d^2} - b^T M^{-1} b)/2\sigma^2} \int_{-\infty}^{\infty} du_1 du_2 e^{-u_1^2 \lambda_1/2\sigma^2} e^{-u_2^2 \lambda_2/2\sigma^2} =$$

$$e^{-(N\overline{d^2} - b^T M^{-1} b)/2\sigma^2} \frac{2\pi\sigma^2}{\sqrt{\det M}}.$$

This leaves only the integration over σ in (15), an expression which can be evaluated using a standard result, see, e.g., M. Abramowitz and I. A. Stegun, *Handbook of Mathematical Functions*, vol. 55 of *Applied Mathematics Series*, National Bureau of Standards, Washington, 1964 (reprinted by Dover Publications, New York, 1968), which is incorporated herein by reference:

$$\int_{-0}^{\infty} dx x^{\alpha-1} e^{-Cx} = \frac{\Gamma(\alpha)}{C^\alpha}. \quad (18)$$

Doing so gives $$P(\omega \mid \partial, \mathcal{J}) \propto \frac{Q^{1-N/2}}{\sqrt{\det M}}, \quad (19)$$

where Q is defined as $Q = N\overline{d^2} - b^T M^{-1} b$.

With the marginal posterior probability as a function of ω alone; for any given data set, the value of ω that maximizes (19), which will be denoted by $\omega_*$, is the frequency that is most consistent with the data and the model. The values of parameters that have been marginalized can be estimated from the corresponding expectation values evaluated at $\omega = \omega_*$. The expectation value of any function Φ of the model parameters is given by $$\langle \varphi \rangle = \frac{\int d\sigma \int dB_1 dB_2 \varphi(\omega; \sigma, B_1, B_2) P(v \mid \partial, \mathcal{J})}{\int d\sigma \int dB_1 dB_2 P(v \mid \partial, \mathcal{J})} \quad (20)$$

For example, an estimate of the phase and quadrature amplitudes is obtained from $$\langle B \rangle = \frac{\int d\hat{B}_1 d\hat{B}_2 (\hat{B} + M^{-1} b) e^{-\hat{B}^T M \hat{B}/2\sigma^2}}{\int d\hat{B}_1 d\hat{B}_2 e^{-\hat{B}^T M \hat{B}/2\sigma^2}} \quad (21)$$

$$= M^{-1} b.$$

By a similar calculation $$\langle B^T B \rangle = b^T M^{-2} b + 2\sigma^2 \frac{N}{\det M} \quad (22)$$

and $$\langle \sigma^2 \rangle = \frac{Q}{N-4}. \quad (23)$$

From (22) the signal-to-noise ratio can be estimated as follows:

$$SNR = \sqrt{2 \frac{N}{\det M} + \frac{\langle B \rangle^T \langle B \rangle}{\langle \sigma^2 \rangle}}, \quad (24)$$

where $\sigma^2$ is approximated by $\langle \sigma^2 \rangle$. Furthermore, the uncertainty in $\omega_*$ can be estimated. From (8) and (16):

$$P(\omega, \sigma \mid \partial, \mathcal{J}) \propto e^{-Q/2\sigma^2}. \quad (25)$$

Expanding Q around $\omega_*$, $$P(\omega, \sigma \mid \partial, \mathcal{J}) \propto e^{-Q''(\omega_*)(\omega - \omega_*)^2/4\sigma^2}. \quad (26)$$

Taking the width of this distribution as a measure of the uncertainty in $\omega_*$ gives $$\Delta\omega_* = \sqrt{\frac{2\langle \sigma^2 \rangle}{Q''(\omega_*)}}, \quad (27)$$

where $\sigma^2$ has again been approximated by $\langle \sigma^2 \rangle$.

As discussed above, Bayesian analysis was applied to the problem of determining the vibration frequency, which is manifest as a modulation of the Doppler shifted laser light. In the experimental arrangement of FIG. 1, the average Doppler frequency was significantly higher than the imposed vibration frequency and well resolved by the sampling rate. For these reasons, it is sufficient to determine the instantaneous Doppler shift using traditional FFT methods. The measured time series is split into a sequence of "windows." After removing any DC component and applying a Bartlett window function, the power spectrum is estimated using the FFT and the frequency corresponding to the maximum power is determined by quadratic interpolation. This process yields a time series of Doppler frequencies with a sample interval corresponding to the window length. It is this derived time series that is then analyzed using the Bayesian methods described above.

Figure 3:
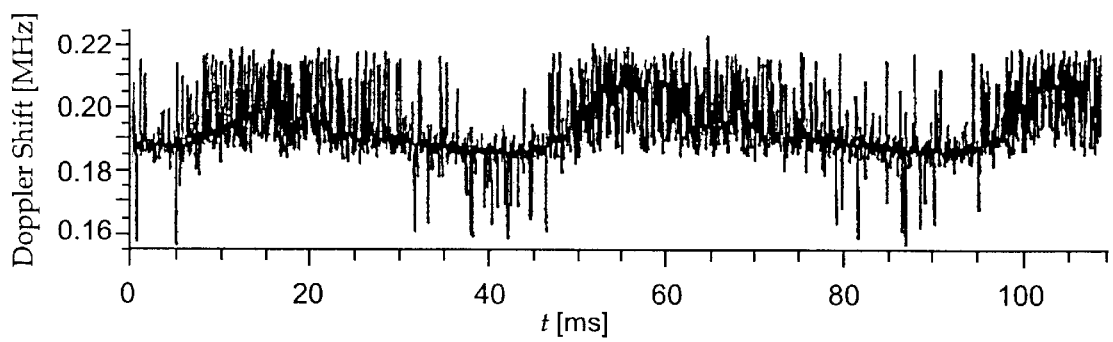
FIG. 3 shows the time series of Doppler shifts determined using the 32 $\mu$s window.

Results for four different length windows: 64, 128, 256, and 512 samples corresponding to 32 μs, 64 μs, 128 μs and 256 μs, respectively, are now presented. FIG. 3 shows the time series of Doppler shifts determined using the 32 μs window. The time series clearly contains a significant stochastic component; however, by eye, a periodic structure can also be discerned. In this application, e does not represent measurement "noise" but rather the stochastic component of the signal, i.e., the signal is considered to be composed of a deterministic part which is modeled by g and a stochastic part, e, which is assumed to have a Gaussian distribution. The statistical arguments are the same as in the case where e corresponds to experimental noise, but the philosophy is slightly different.

The time series of Doppler shifts is analyzed as follows:
1) The average of the data set is computed and an offset is added to the data to yield a new data set that has zero average.
2) The marginal posterior probability, given by (19) is then computed and co is found that maximizes this probability. The specific procedure is to first bracket the $\omega_*$ using a standard technique such as disclosed in "Numerical Recipes in C, The Art of Scientific Computing" W.H. Press, S. A. Teukolsky, W. T. Vetterling and B. P. Flannery, Second Edition, Cambridge University Press, Cambridge (1992), which is incorporated herein by reference. A tolerance is chosen, typically $10^{-9}$ and $\omega_*$ is computed by minimizing the negative of the probability employing the method disclosed in R. P. Brent, "Algorithms for Minimization without Derivatives," Englewood Cliffs, N.J.: Prentice-Hall (1973), which is incorporated herein by reference. This method is chosen because it is quadratically convergent and does not require derivatives of the probability function. The harmonic amplitudes are computed using (21) and the uncertainty in $\omega_*$ is computed using (27). This procedure identifies the dominant sinusoidal component in the time series of Doppler shifts.

3) Additional frequencies can be extracted by repeating this procedure. To do so, one first computes a residual which is given by $$r_j = d_j - B_1 \cos(\omega t_j) - B_2 \sin(\omega t_j) - d_{AVG}$$

where $d_{AVG}$ is the average of the data set computed in step 1. This residual takes the place of the original time series and the computation of steps 1 through 3 are repeated until the posterior probability is devoid of significant features.

Figures 4A, 4B, 4C, 4D, 4E, 4F:
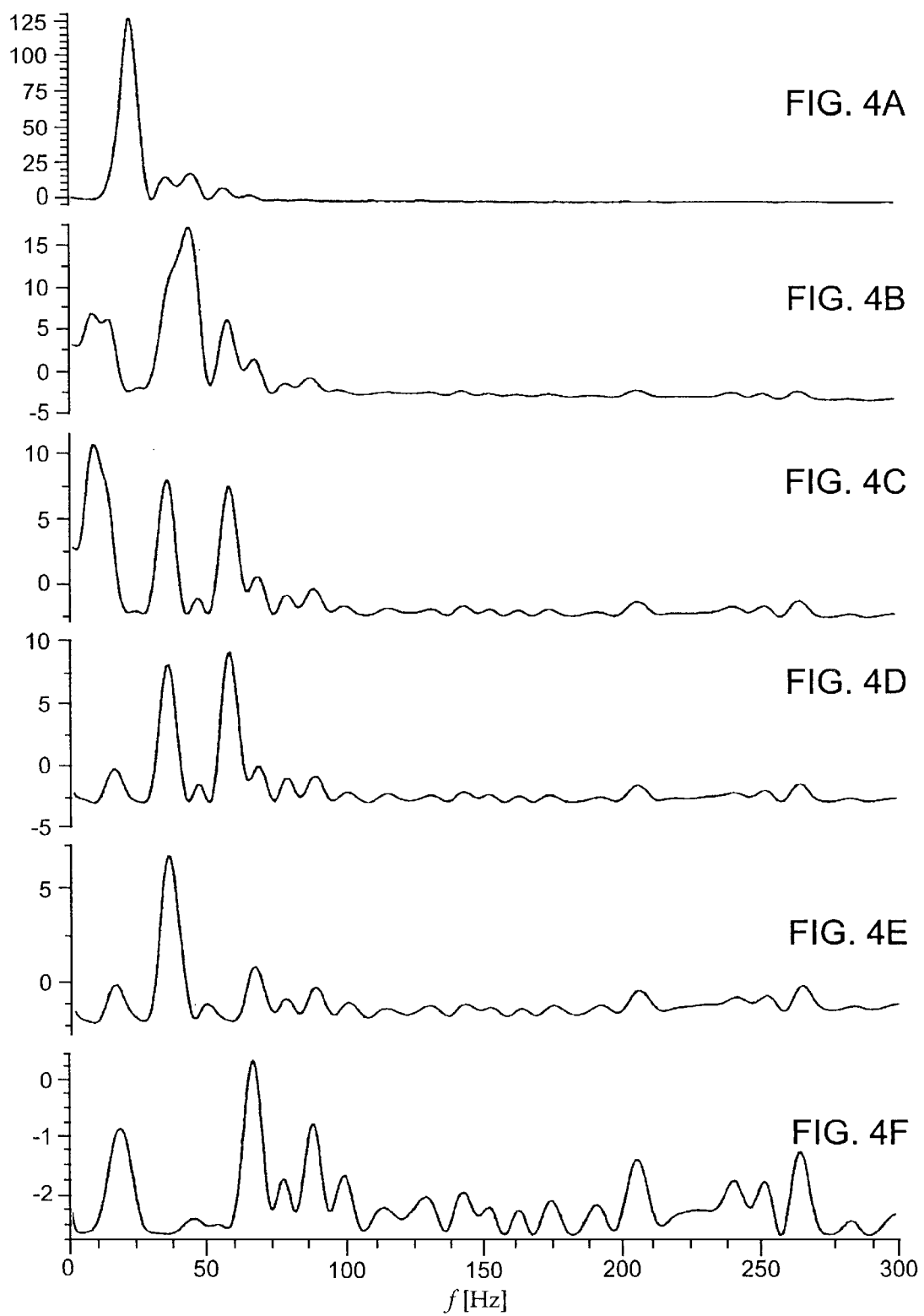
FIGS. 4A–4F show posterior probability plots for an original signal (FIG. 4A) and a sequence of residuals (FIGS. 4B–4F), each showing probability after removing the dominant frequency of the previous panel.
Figure 6A:
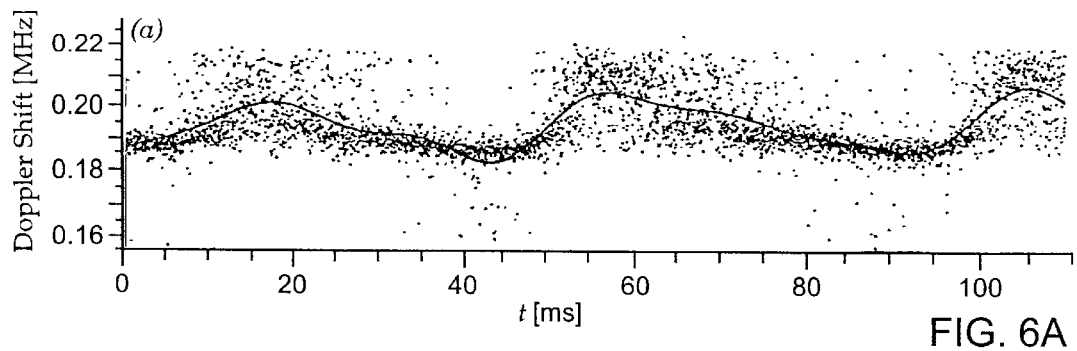
FIGS. 6A–6D are plots showing best fit (solid line) and raw time series (dots) using various window sizes; the best fits corresponding to the parameters shown in FIGS. 5A–5D, respectively.
Figure 6B:
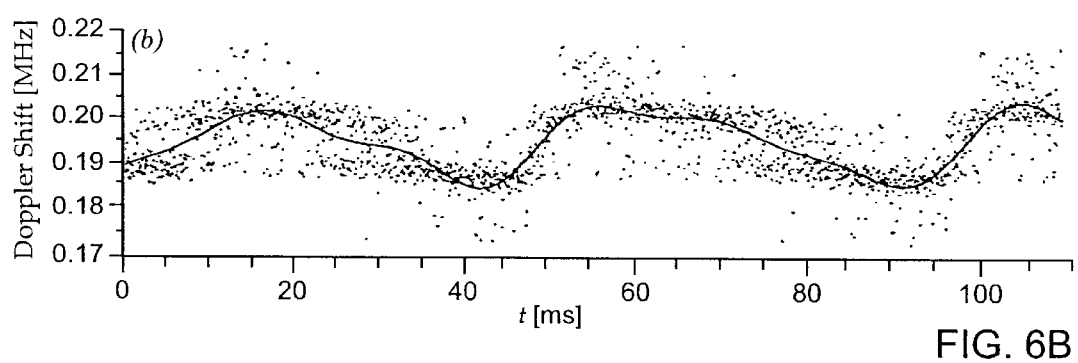
Figure 6C:
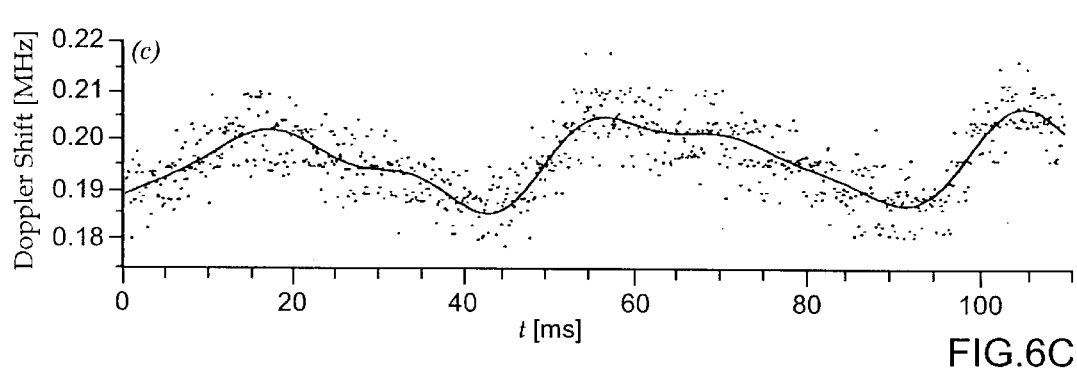
Figure 6D:
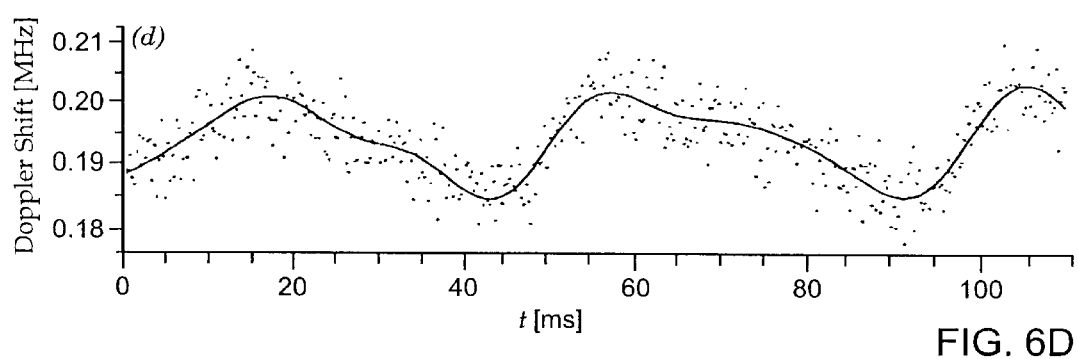

FIGS. 4A–4F show posterior probability plots for an original signal (FIG. 4A) and a sequence of residuals (FIGS. 4B–4F), each showing probability after removing the dominant frequency of the previous panel. More specifically, FIG. 4A is a plot of $\log_{10}$, $P(\omega|e,\Im)$ as given by (19) for the Doppler signal obtained from the 128 µs window vs. $f(\omega = 2\pi f)$ for the original signal. As can be seen from the plot, the peak in the probability is vastly above the background level, which gives rise to precise estimates of the parameters. The probability plot suggests the presence of other frequencies in addition to that responsible for the main peak. Although the model only contains a single frequency, multi-harmonic time series can be analyzed by iteratively removing the frequency corresponding to the peak in the probability and then re-analyzing the residual. This approach works well with sinusoidal signals. See, J. J. K. Ó Ruanaidh and W. J. Fitzgerald, *Numerical Bayesian Methods Applied to Signal Processing*, Springer, New York, 1996, which is incorporated herein by reference. A more complete approach is to carry out a full multi-mode analysis, using $P(\partial|\Im)$ to select the optimal model. Such an analysis is significantly more computationally intensive than the recursive method used here. As demonstrated below, the results from this simpler approach are of sufficiently high quality that the more complex multi-mode method is not justified by this data.

Shown in FIGS. 4B–4F are posterior probabilities of the residual after removal of subsequent frequencies. The vertical scale changes drastically; as each frequency is removed, the peak in the probability corresponding to the "next" frequency is much smaller relative to the background. These additional frequencies are attributed to (i) harmonics of the drive modulation frequency due to the "accelerate and coast" effect of the drive modulation and (ii) motor "cogging" effects due to the low chopper wheel velocity. By FIG. 4F, the probability no longer contains any dominant features.

The results of this procedure, frequency and amplitude estimates, for all four window sizes are summarized in FIGS. 5A–5D, respectively. The frequencies are extracted from the signal sequentially as described above and the uncertainties are computed using (27) and the amplitudes are obtained using (22).

For the three largest windows (FIGS. 5B–5D), the frequency estimates are in complete agreement within their respective one-σ uncertainties. The results from the 32 µs window are also in agreement with the other cases except for the frequency of the mode near 22 Hz. This (small) discrepancy is attributed to the fact that the window length of 32 µs is smaller than the speckle induced decoherence time of approximately 40 µs. Thus, for this short window, the stochastic component may deviate significantly for the Gaussian distribution that it achieves over longer time intervals. This has the effect of making the model not quite correct, i.e., the assumptions made about the "noise" statistics are not valid. Thus, there may be some disagreement with the cases where the model more closely matches the data.

FIGS. 6A–6D are plots showing best fit (solid line) and raw time series (dots) using (a) 32 µs, (b) 64 µs, (c) 128 µs, and (d) 256 µs windows. The best fits correspond to the parameters shown in FIGS. 5A–5D, respectively.

Figure 7:
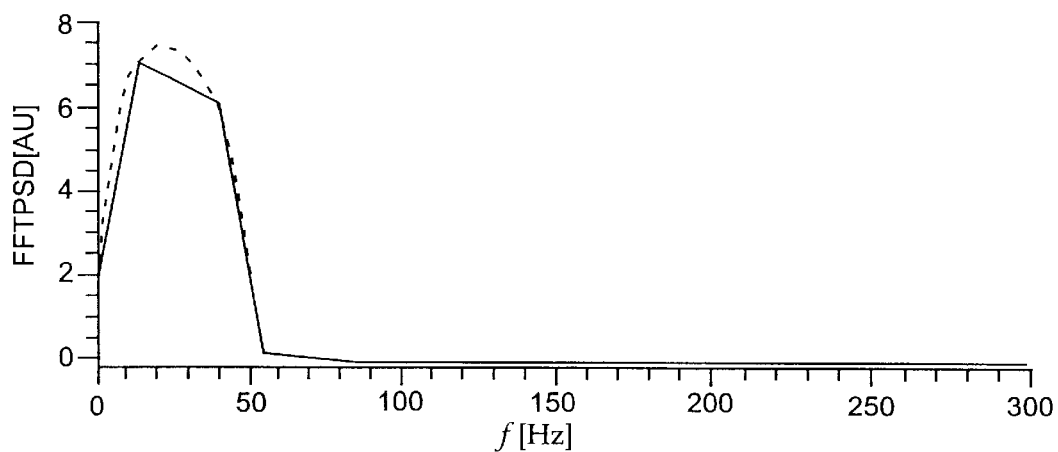
FIG. 7 illustrates the FFT estimate of the Power Spectral Density (PSD) of the time series produced using the 256 $\mu$s window.

By way of comparison, FIG. 7 illustrates the FFT estimate of the Power Spectral Density (PSD) of the time series produced using the 256 µs window. The vibration power spectral density estimated using FFT (solid line) and cubic interpolation of the peak (dashed line) are both shown. The PSD has a maximum at f=20.6 Hz with a Half Width at Half Maximum (HWHM) of 17.5 Hz. This maximum value is approximately 1.2 Hz below the average frequency for this mode determined from the Bayesian analysis. Clearly, the PSD is incapable of resolving the multiple frequencies contained in the vibration signal. While the peak (after interpolation) yields approximately the same value for the best vibration frequency, the significant width of the spectrum (due to the small number of periods contained in the time series) makes an accurate estimate of the frequency difficult. Contrary to popular belief, "enlarging" the data set by zero-padding does not improve the resolution of the FFT but merely interpolates the power spectrum between the frequencies of the shorter data set. The width of this power spectrum estimate is a fundamental limitation of using the FFT and cannot be avoided.

The foregoing demonstrates the power of Bayesian analysis according to the present invention when dealing with a short time series containing a significant stochastic component. The Bayesian approach yields significantly more precise frequency estimates than are possible when using the FFT as a spectral estimator. The foregoing demonstrates that it is important that the model accurately fit the data as this is part of the "prior information." As with the priors for the noise or the other model parameters, choosing a poor model can color the results of the analysis. Ultimately, the parameter values are sought which, given the model, are most consistent with the data. The Bayesian framework provides a means of selecting between competing models; and often a complete analysis should include consideration of multiple models. Even considering only a single sinusoid model (as discussed above), the Bayesian approach yields a frequency estimate that is accurate to approximately 1%. Given the short time series, this is nonetheless quite impressive as it represents a significant improvement (by nearly two orders of magnitude) upon the estimate obtained from the FFT.

The method of the present invention is expected to have the greatest impact in situations where measurement dwell-time is at a premium, such as vibrational imaging (See, P. Lutzmann, R. Frank, and R. Ebert, "Laser radar based vibration imaging of remote objects," in *Laser Radar Technology and Applications V, Proc. SPIE*, G. W. Kamerman, U. N. Singh, C. Werner, and V. V. Molebny, eds., vol. 4035, pp. 436–443, SPIE, (Bellingham, Wash.), 2000, incorporated herein by reference) where many points across the surface of an object must be monitored sequentially during a measurement period, or in situations where the vibrational character is rapidly changing and dwell-time must be limited. If the experimental circumstances are such that there is not such a large separation between the Doppler frequency and the vibration frequency, then using such large windows for determining the Doppler frequency would not be appropriate. In such a case, Bayesian analysis can also be used to determine the Doppler shift. While not necessary with the data considered here, the Bayesian methods of the present invention should allow for resolving vibration frequencies that are a significant fraction of the Doppler frequency.

Although the present invention has been described in terms of the preferred embodiment above, numerous modifications and/or additions to the above-described preferred embodiment would be readily apparent to one skilled in the art. It is intended that the scope of the present invention extends to all such modifications and/or additions.

We claim:

1. A laser vibrometry method comprising the steps of:
   employing a laser to generate laser vibrometry data for a system under observation;
   performing Bayesian parameter estimation calculations for a mathematical model of the system under observation, the laser vibrometry data and prior information to generate estimations of parameters of the mathematical model;
   evaluating the estimations of parameters; and
   if desired or necessary, repeating the step of performing Bayesian parameter estimation calculations with a different model and/or different laser vibrometry data.

2. The laser vibrometry method of claim 1, wherein the system under observation comprises a reflective target in motion.

3. The laser vibrometry method of claim 1, wherein the laser vibrometry data comprises continuous wave (CW) laser vibrometry data.

4. The laser vibrometry method of claim 1, wherein the laser vibrometry data comprises dual pulse coherent laser vibrometry data.

5. The laser vibrometry method of claim 1, wherein the laser vibrometry data comprises vibrational imaging data.

6. The laser vibrometry method of claim 1, wherein the prior information comprises noise information.

7. The laser vibrometry method of claim 6, wherein the noise information pertains to a signal-to-noise ratio.

8. The laser Vibrometry method of claim 6, wherein the noise information is assigned a least informative probability density.

9. The laser vibrometry method of claim 1, wherein the step of evaluating parameter estimation results includes evaluating vibration frequencies.

10. The laser vibrometry method of claim 1, wherein the step of evaluating parameter estimation results includes evaluating variances of parameter estimates.

11. The laser vibrometry method of claim 1, wherein the step of evaluating parameter estimation results includes evaluating higher order moments.

12. The A laser vibrometry method comprising the steps of:
    creating one or more mathematical models of a system under observation;
    employing a laser to generate laser vibrometry data for the system under observation;
    processing the one or more mathematical models, the laser vibrometry data and prior information employing a statistical signal processing technique to generate estimates of parameters for the one or more mathematical models;
    performing an evaluation of the parameter estimations; and
    if results of the evaluation are determined not to be satisfactory, repeating the processing step with a different model and/or different laser vibrometry data.

13. The laser vibrometry method of claim 12, wherein the statistical signal processing technique comprises a Bayesian processing technique.

14. The laser vibrometry method of claim 12, wherein the one or more mathematical models are models of the system under observation.

* * * * *